(12) United States Patent
Riehl

(10) Patent No.: US 7,601,115 B2
(45) Date of Patent: Oct. 13, 2009

(54) SEIZURE THERAPY METHOD AND APPARATUS

(75) Inventor: Mark Edward Riehl, Doylestown, PA (US)

(73) Assignee: Neuronetics, Inc., Malvern, PA (US)

(*) Notice: Subject to any disclaimer, the term of this patent is extended or adjusted under 35 U.S.C. 154(b) by 929 days.

(21) Appl. No.: 10/852,349

(22) Filed: May 24, 2004

(65) Prior Publication Data
US 2005/0261542 A1 Nov. 24, 2005

(51) Int. Cl.
*A61N 1/00* (2006.01)
(52) U.S. Cl. .................................................. 600/14
(58) Field of Classification Search ............... 600/9–15; 128/897, 898
See application file for complete search history.

(56) References Cited

U.S. PATENT DOCUMENTS

| | | | |
|---|---|---|---|
| 3,658,051 A | 4/1972 | Maclean | |
| 3,683,923 A | 8/1972 | Anderson | |
| 4,601,753 A | 7/1986 | Soileau et al. | |
| 4,712,558 A | 12/1987 | Kidd et al. | |
| 4,940,453 A | 7/1990 | Cadwell | |
| 4,994,015 A | 2/1991 | Cadwell | |
| 4,995,395 A | 2/1991 | Ilmoniemi et al. | |
| 5,047,005 A | 9/1991 | Cadwell | |
| 5,061,234 A | 10/1991 | Chaney | |
| 5,078,674 A | 1/1992 | Cadwell | |
| 5,097,833 A | 3/1992 | Campos | |
| 5,116,304 A | 5/1992 | Cadwell | |
| 5,299,569 A | 4/1994 | Wernicke et al. | |
| 5,707,334 A | 1/1998 | Young | |
| 5,766,124 A | 6/1998 | Polson | |
| 5,769,778 A | 6/1998 | Abrams et al. | |
| 5,813,970 A * | 9/1998 | Abrams et al. | 600/14 |
| 6,057,373 A | 5/2000 | Fogel | |
| 6,066,084 A | 5/2000 | Edrich et al. | |
| 6,117,066 A | 9/2000 | Abrams et al. | |
| 6,132,361 A * | 10/2000 | Epstein et al. | 600/13 |
| 6,155,966 A | 12/2000 | Parker | |
| 6,169,963 B1 | 1/2001 | Markov | |
| 6,179,769 B1 | 1/2001 | Ishikawa et al. | |
| 6,179,770 B1 | 1/2001 | Mould | |
| 6,179,771 B1 | 1/2001 | Mueller | |

(Continued)

FOREIGN PATENT DOCUMENTS

EP 1 273 230 A1 1/2003

(Continued)

OTHER PUBLICATIONS

Garcia-Toro, M. et al., "Modest Adjunctive Benefit with Transcranial Magnetic Stimulation in Medication-Resistant Depression", *Journal of Affective Disorders*, 2001, 64, 271-275.

(Continued)

*Primary Examiner*—Samuel G Gilbert

(57) ABSTRACT

The invention provides a method for treating a patient for mental illnesses, such as depression, by applying a magnetic field to the patient, producing a seizure in the patient as a function of a strength of the magnetic field, and preventing further stimulation from the magnetic field when the seizure is in progress. Such Magnetic Seizure Therapy (MST) does not include many of the known side effects of electroconvulsive therapy (ECT).

54 Claims, 3 Drawing Sheets

U.S. PATENT DOCUMENTS

| | | |
|---|---|---|
| 6,198,958 B1 | 3/2001 | Ives et al. |
| 6,253,109 B1 | 6/2001 | Gielen |
| 6,256,531 B1 | 7/2001 | Ilmoniemi et al. |
| 6,266,556 B1 | 7/2001 | Ives et al. |
| 6,366,814 B1 | 4/2002 | Boveja et al. |
| 6,389,318 B1 | 5/2002 | Zarinetchi et al. |
| 6,402,678 B1 | 6/2002 | Fischell et al. |
| 6,463,328 B1 | 10/2002 | John |
| 6,480,743 B1 | 11/2002 | Kirkpatrick et al. |
| 6,484,059 B2 | 11/2002 | Gielen |
| 6,488,617 B1 | 12/2002 | Katz |
| 6,497,648 B1 | 12/2002 | Rey |
| 6,503,187 B1 | 1/2003 | Ilmoniemi et al. |
| 6,537,197 B1 | 3/2003 | Ruohonen et al. |
| 6,551,233 B2 | 4/2003 | Perreault et al. |
| 6,560,490 B2 | 5/2003 | Grill et al. |
| 6,567,702 B1 | 5/2003 | Nekhendzy et al. |
| 6,572,528 B2 | 6/2003 | Rohan et al. |
| 6,591,138 B1 | 7/2003 | Fischell et al. |
| 6,629,935 B1 | 10/2003 | Miller et al. |
| 6,663,556 B2 | 12/2003 | Barker |
| 6,827,681 B2 | 12/2004 | Tanner et al. |
| 6,849,040 B2 | 2/2005 | Ruohenen et al. |
| 6,978,179 B1 | 12/2005 | Flagg et al. |
| 2001/0031906 A1 | 10/2001 | Ishikawa et al. |
| 2002/0013612 A1 | 1/2002 | Whitehurst |
| 2002/0087201 A1 | 7/2002 | Firlik et al. |
| 2002/0091419 A1 | 7/2002 | Firlik et al. |
| 2002/0103515 A1 | 8/2002 | Davey et al. |
| 2002/0123780 A1 | 9/2002 | Grill et al. |
| 2002/0160436 A1 | 10/2002 | Markov et al. |
| 2002/0169355 A1 | 11/2002 | Rohan et al. |
| 2003/0004392 A1 | 1/2003 | Tanner et al. |
| 2003/0023159 A1 | 1/2003 | Tanner |
| 2003/0028072 A1 | 2/2003 | Fischell et al. |
| 2003/0050527 A1 | 3/2003 | Fox et al. |
| 2003/0073899 A1 | 4/2003 | Ruohonen et al. |
| 2003/0074032 A1 | 4/2003 | Gliner et al. |
| 2003/0082507 A1 | 5/2003 | Stypulkowski |
| 2003/0087264 A1 | 5/2003 | Kaplitt et al. |
| 2003/0088274 A1 | 5/2003 | Gliner et al. |
| 2003/0097161 A1 | 5/2003 | Firlik et al. |
| 2003/0125786 A1 | 7/2003 | Gliner et al. |
| 2003/0130706 A1 | 7/2003 | Sheffield et al. |
| 2003/0195588 A1 | 10/2003 | Fischell et al. |
| 2003/0204135 A1 | 10/2003 | Bystritsky |
| 2004/0010177 A1 | 1/2004 | Rohan et al. |
| 2004/0077921 A1 | 4/2004 | Becker et al. |
| 2004/0127942 A1 | 7/2004 | Yomtov et al. |
| 2004/0138550 A1 | 7/2004 | Hartlep et al. |
| 2004/0143300 A1 | 7/2004 | Rogers |
| 2005/0021104 A1 | 1/2005 | DiLorenzo |
| 2005/0124848 A1 | 6/2005 | Holzner |
| 2005/0216071 A1 | 9/2005 | Devlin et al. |
| 2005/0228209 A1 | 10/2005 | Schneider et al. |
| 2005/0256539 A1 | 11/2005 | George et al. |

FOREIGN PATENT DOCUMENTS

| | | |
|---|---|---|
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/085454 A1 | 10/2002 |
| WO | WO 02/854449 A2 | 10/2002 |
| WO | WO 02/089902 A3 | 11/2002 |
| WO | WO 02/094997 A2 | 11/2002 |
| WO | WO 03/035163 A2 | 5/2003 |
| WO | WO 03/039468 A2 | 5/2003 |
| WO | WO 03/082405 A1 | 10/2003 |
| WO | WO 03/084605 A1 | 10/2003 |
| WO | WO 03/085546 A1 | 10/2003 |
| WO | WO 03/090604 A2 | 11/2003 |
| WO | WO 03/098268 A1 | 11/2003 |
| WO | WO 2004/006750 A2 | 1/2004 |
| WO | WO 2004/082759 A2 | 9/2004 |
| WO | WO 2004/100765 A2 | 11/2004 |
| WO | WO 2005/000401 A1 | 1/2005 |
| WO | WO 2005/065768 A1 | 7/2005 |

OTHER PUBLICATIONS

George, M.S. "New Methods of Minimally Invasive Brain Modulation as Therapies in Psychiatry: TMS,MST,VNS and DBS", *Chinese Medical Journal* (Taipei), 2002, 65, 349-360.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lisanby, S.H. MD. et al., "Magnetic Seizure Therapy of Major Depression", *Arch Gen Psychiatry*, 2001, 58, 303-307.

Lisanby, S.H., "Update on Magnetic Seizure Therapy: A Novel Form of Convulsive Therapy", *The Journal of ECT*, 2002, 18, 182-188.

Terrace, H.S. et al., "The Cognitive Effects of Electroconvulsive Shock and Magnetic Seizure Therapy in Rhesus Monkeys", *Society for Neuroscience Abstract Viewer and Itinerary Planner*, 2002, Abstract Only # 184.14.

Terrace, H.S. et al., "The Cognitive Effects of Electroconvulsive Shock Stimulation and Magnetic Seizure Therapy in Rhesus Monkeys", *Society for Neuroscience Abstracts*, 2001, 27(1), 536.7, p. 1418.

Pridmore, S., "Substitution of Rapid Transcranial Magnetic Stimulation Treatments for Electroconvulsive Therapy Treatments in a Course of Electroconvulsive Therapy", *Depression and Anxiety*, 2000, 12, 118-123.

Roth, Y. et al., "A Coil Design for Transcranial Magnetic Stimulation of Deep Brain Regions", *Journal of Clinical Neurophysiology*, 2002, 19(4), 361-370.

Trivedi, M.H., MD., "Treatment-Resistant Depression: New Therapies on the Horizon", *Annals of Clinical Psychiatry*, 2003, 15(1), 59-70.

Hess, C.W. et al., "Magnetic Stimulation of the Human Brain: Influence of Size and Shape of the Stimulating Coil", *Motor Disturbances II*, 1990, 3, 31-42.

Wassermann, E.M., "Repetitive Transcranial Magnetic Stimulation: An Introduction and Overview", *CNS Spectrums, The International Journal of Neuropsychiatric Medicine*, Jan. 1997, 7 pages.

* cited by examiner

Fig. 1
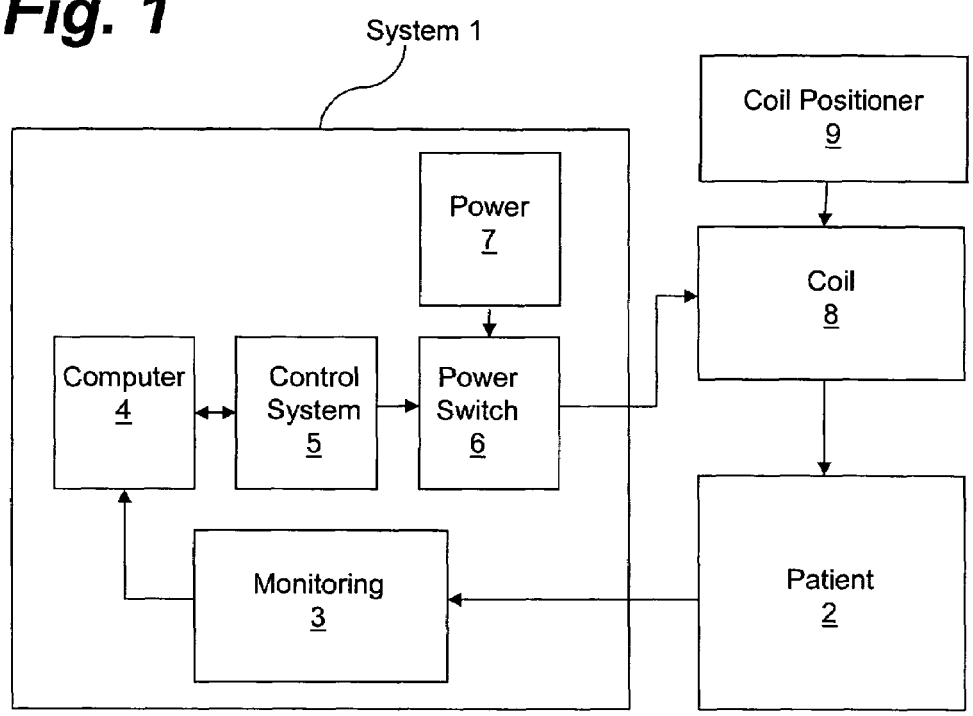
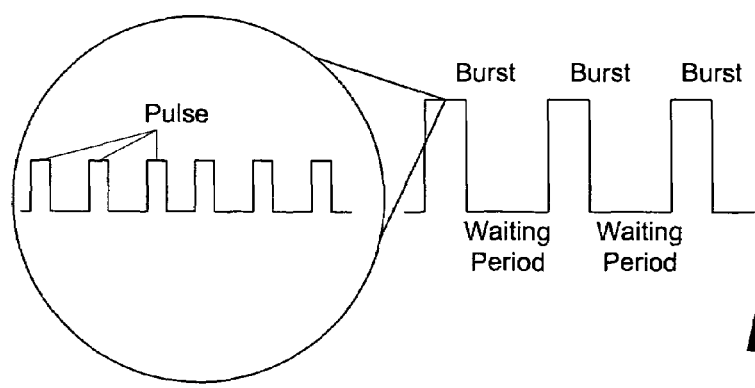
Fig. 2

SEIZURE THERAPY METHOD AND APPARATUS

FIELD OF THE INVENTION

The invention relates to methods of treatment of depression and other maladies. More specifically, the invention relates to the use of seizure therapy for the treatment of depression and other maladies.

BACKGROUND OF THE INVENTION

Severe mental illness may be treated psychoanalytically, pharmacologically, or directly, by stimulation of the brain. The two most popular types of direct stimulation are electric stimulation and magnetic stimulation. In either case, the stimulation may be relatively mild or of a sufficient intensity to cause a seizure. As is well known to those of skill in the art, a seizure may be particularly efficacious in the treatment of some mental illnesses.

For example, electroconvulsive therapy ("ECT") is a treatment for severe mental illness in which a brief application of electric stimulus is used to produce a generalized seizure in a patient. The National Institutes of Health in conjunction with the National Institute of Mental Health convened a Consensus Development Conference on Electroconvulsive Therapy on Jun. 10-12, 1985. The consensus reached was that ECT was efficacious for depression (delusional and severe endogenous), acute manic episodes, and certain types of schizophrenia. Thus, researchers have established the effectiveness of ECT. However, ECT has been shown to be associated with cognitive deficits including memory loss. Moreover, a certain social stigma exists with respect to ECT.

Magnetic seizure therapy ("MST") is a much newer treatment for severe mental illness, but with theoretically comparable results to ECT. Like ECT, MST causes a generalized seizure, with relief presumably occurring by the same biomedical pathways. However, in a critical difference from ECT, MST uses a brief application of a switching magnetic field to provide the stimulus which produces the generalized seizure via electromagnetic induction. This has a variety of benefits, including 1) magnetic fields penetrate tissue without dissipation of energy through conductance; 2) the brain stimulation can be more accurately and reliably dosed; and 3) stimulation can be limited to the brain structures essential for treatment response, thus reducing side-effects associated with ECT, such as memory impairment. (See Lisanby S H, Luber B, Schlaepfer T E, Sackeim H A, *Safety and feasibility of magnetic seizure therapy (MST) in major depression: randomized within-subject comparison with electroconvulsive therapy*. Neuropsychopharmacology. 2003 October, 28 (10): 1852-65. Abstract stating "Compared to ECT, MST seizures had shorter duration, lower ictal EEG amplitude, and less postictal suppression. Patients had fewer subjective side effects and recovered orientation more quickly with MST than ECT. MST was also superior to ECT on measures of attention, retrograde amnesia, and category fluency.")

The invention is directed to improved methods of MST, and hence methods of treatment for severe mental illness.

SUMMARY OF THE INVENTION

The invention provides a system for performing magnetic seizure therapy on a patient, comprising a power switch for applying a pulse of electrical current to a magnetic coil such that the induced current density in the patient's cortex is sufficient to cause a seizure in the patient, a monitoring system for monitoring the patient, and a control system for preventing further stimulation when a seizure is in progress.

The invention also provides a method for treating a patient, comprising applying a magnetic field to the patient, wherein the strength of the field and switching rate is sufficient to produce a seizure in the patient, and preventing further stimulation from the field when a seizure is in progress.

These and other aspects of the invention will become more apparent from the description and claims.

BRIEF DESCRIPTION OF THE DRAWINGS

FIG. 1 is a schematic of a system for performing magnetic seizure therapy in accordance with the invention;

FIG. 2 is a schematic of a method of performing magnetic seizure therapy in accordance with the invention;

DETAILED DESCRIPTION OF ILLUSTRATIVE EMBODIMENTS

Figure 3:
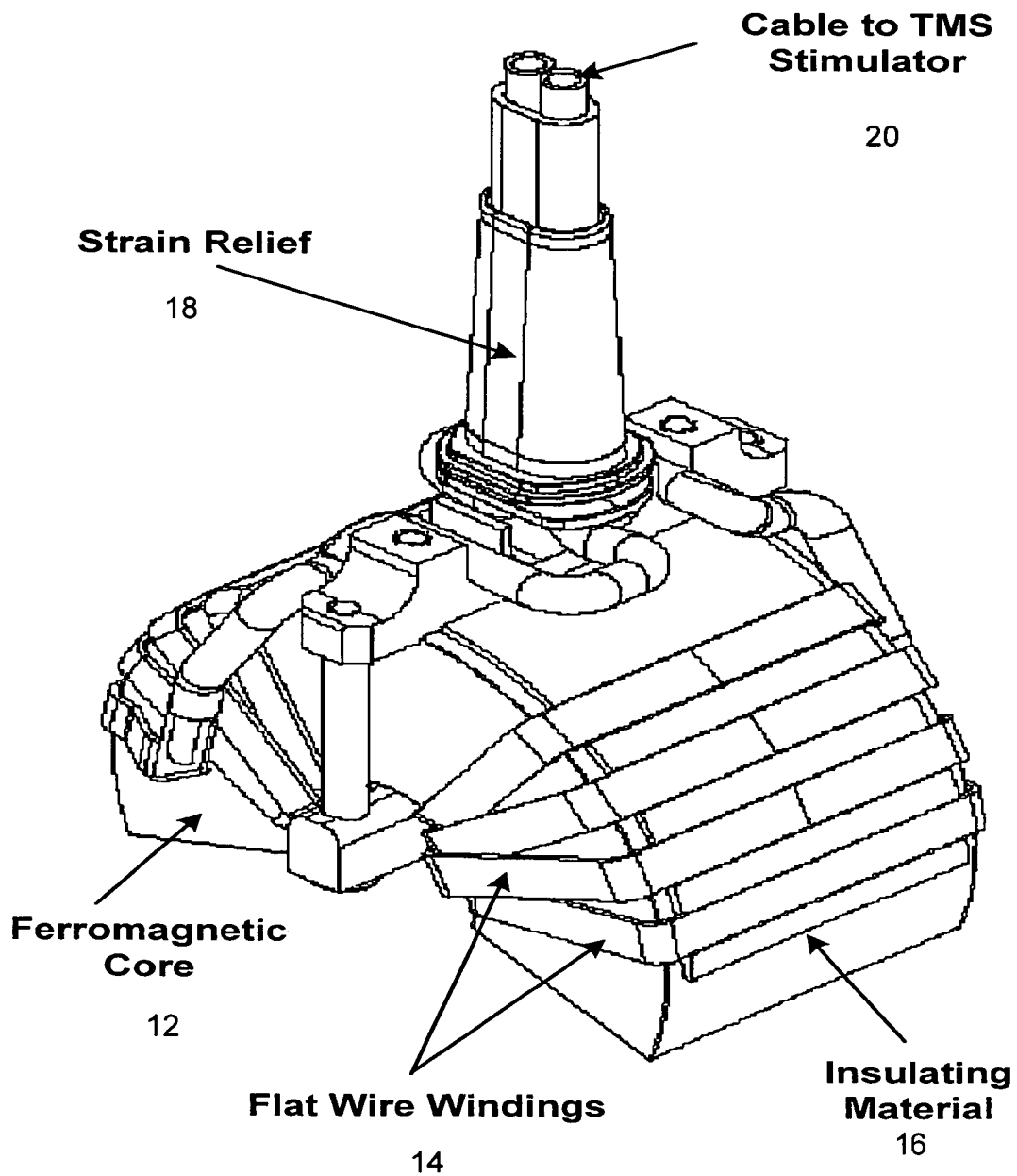
FIG. 3 is a perspective view of a device containing a magnetic coil for producing a magnetic field.

The invention includes a method for performing magnetic seizure therapy on a patient in need thereof, comprising inducing a seizure in the patient, and monitoring the patient to determine certain seizure parameters.

Referring to FIG. 1, a system of the invention is given the reference numeral 1. Such a system is used for performing magnetic seizure therapy on a patient 2 in need thereof.

The method and apparatus of the invention are used to treat a patient such as a human suffering from major depressive disorder, epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (panic disorder w and w/o agoraphobia, social phobia also known as social anxiety disorder, acute stress disorder, generalized anxiety disorder), post-traumatic stress disorder (one of the anxiety disorders in DSM), obsessive compulsive disorder (one of the anxiety disorders in DSM), pain (migraine, trigeminal neuralgia) (also: chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury & regeneration/rehabilitation, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, or eating disorders (bulimia, anorexia, binge eating).

As will be described, the system 1 comprises a monitoring system 3, a computer 4, a control system 5, a power switch 6, and a power source 7.

Magnetic Seizure Therapy

It is known that seizures are effective for treating major depressive disorders, delusional depression, severe endogenous depression, acute manic episodes, and short duration, acute onset, intense affective symptom schizophrenia. Moreover, it is well known to those skilled in the art that MST has fewer negative side effects than ECT or medications.

The magnitude of an electric field induced in a conductor is proportional to the rate of change of magnetic flux density that cuts across the conductor. Faraday's law, well known to those skilled in the art, may be represented as E~–(dB/dt), where E is the induced electric field in volts/meter, and dB/dt is the time rate of change of magnetic flux density in Tesla/second. In other words, the amount of electric field induced in an object like a conductor is determined by two factors: the magnetic flux density and the time rate of change of the flux density. The greater the flux density and its derivative, the greater the induced electric field and resulting current density. In the context of electrical stimulation of the anatomy, certain parts of the anatomy (e.g., nerves, tissue, muscle, brain) act as a conductor and carry electric current when an electric field is presented. The electric field may be presented to these parts of the anatomy transcutaneously by applying a time varying (e.g., pulsed) magnetic field to the portion of the body. For example, a time-varying magnetic field may be applied across the skull to create an electric field in the brain tissue, which produces a current. If the induced current is of sufficient density, neuron membrane potential may be reduced to the extent that the membrane sodium channels open and an action potential response is created.

In one embodiment, the system 1 is used to supply rapidly changing magnetic flux which creates electric fields, thereby inducing electrical currents in the patient 2. Because the magnetic flux density decreases in strength as the square of the distance from the source of the magnetic field, the flux density is greater the closer the conductor is to the source of the magnetic field.

Turning to FIG. 2, in operation, by applying a pulse of electrical current ("pulse") to the coil, a magnetic field is developed. By varying the pulse, an electric field is induced. Induced current densities of about 10-15 milli-amperes/cm$^2$ or greater are sufficient to depolarize neurons. Induced current densities of about 20 milli-amperes/cm$^2$ to about 45 milli-amperes/cm$^2$ at known cortical locations are capable of inducing seizures in humans.

The pulse may be applied in a pulse train, also referred to in the art as a "burst." The burst depends on the number of pulses, the pulse width, and the time applied. These parameters may also be expressed by frequency (pulses/sec). In general, a frequency in a range of about 40 to about 60 Hertz over a range of about 2 to about 8 seconds is desired for an MST burst. A pulse width may be about 500 microseconds.

In an alternative embodiment, the frequency is in a range from about 20 to about 120 Hertz.

Application of the burst is followed by onset of the seizure or, if the stimulus was insufficient, a waiting period. The waiting period is governed by the time required to allow the coil to cool, the capacitor to recharge, and physiological recovery time. In one embodiment, heat is generated by resistive loss in the coil by the pulse burst, and no portion of the device exceeding approximately 42° C. can be allowed to touch the patient, thus requiring the coil to cool down before another burst is applied. Thus, the waiting period may typically be set to a fixed interval of one minute to guarantee that conditions are appropriate before triggering the next pulse burst.

In one embodiment, the waiting period is less than one minute. More efficient coils (i.e. lower resistive losses and lower required current) assure that some embodiments of the invention allow waiting periods as short as 15-20 seconds.

The capability of applying stimulation bursts more rapidly than once per minute is accomplished by use of the more efficient ferromagnetic coil and system intelligence within the control system that considers capacitor charge times and coil heating characteristics. The system provides a variable trigger delay that is minimized, while still considering the above limiting parameters. In addition, coil heating is significantly less with a ferromagnetic core design since only approximately one half the current is required to attain an equivalent magnet field intensity compared to an air core coil design. This reduces resistive heating by the square of the current applied.

Monitoring System

As illustrated in FIG. 1, a monitoring system 3 is provided for monitoring the patient. Monitoring may include using conventional electroencephalogram ("EEG") methods or a subset thereof. EEG can be used to determine when the seizure starts and stops. Typically, an MST-induced seizure lasts about 20 seconds. In comparison, an ECT-induced seizure can last about 120 seconds. The EEG monitoring may need only involve 3-6 leads. EEG can also be used to monitor cortical excitability between bursts (i.e. alpha wave activity).

In one embodiment, an EEG monitor is provided which utilizes a small number (e.g. 3-6) of lead wires and electrodes attached to the patient. One skilled in the art is aware that steps must be taken that the electrodes or lead wires do not conduct significant eddy currents that could be induced by the pulsed magnetic field. In one embodiment, this is accomplished by using high impedance designs, minimal conductive cross sections, or placing the electrodes in positions where the magnetic field is not of concern. The EEG monitor provides the operator and the MST system with information regarding the seizure status of the patient, for example, alpha waves can indicate if the patient is in a normal resting state, pre-seizure state, seizure in progress, returned to resting state (post-seizure).

This information is highly desirable, such as for "locking out" pulsing while a seizure is in progress or to indicate if the applied power level was sufficient to induce the desired seizure. Locking out refers to stopping or preventing further simulation. Such lock out directions may provide for a manual override, or may not in other embodiments. Locking out includes interrupting the flow of current to the coil, blocking or shielding the patient from the magnetic field, or moving the coil a sufficient distance away from the patient to prevent stimulation.

In addition, the EEG may be used to gauge cortical excitability before the first pulse burst and between attempts. This provides the capability to step up the power levels of successive pulse bursts in a predictive manner in order to reach the level required to induce a seizure. By accounting for changes of cortical excitability, this can minimize the number of attempts required which shortens the procedure and exposes the patient to fewer unnecessary stimulations. Unnecessary stimulation artificially raises the cortical excitability level, eventually requiring higher stimulation power to achieve the desired seizure.

Furthermore, monitoring may include using electrocardiogram ("ECG") methods to detect any atypical cardiac responses to treatment, such as cardiac arrthymias or other anomalies requiring clinical intervention.

Monitoring also may include using conventional methods to monitor blood pressure (NIBP) and or heart rate (HR).

Computer and Control System

The system 1 further includes a computer 4. The computer comprises a user interface, such as a display, as well as system intelligence, such as a central processor.

A control system 5 is provided as part of the system 1. The control system 5 comprises devices or logic for monitoring status, determining safety limits, recording treatment parameters, changing machine state (such as between standby, calibration, motor threshold, treatment, and service modes), initiating and terminating treatment, and performing system diagnostics.

In one embodiment, controls are operated manually. In this embodiment, a knowledgeable operator is necessary to prevent firing the coil while the patient is already having a seizure and to estimate the dosage required to induce a seizure.

In another embodiment, the system integrates therapy, monitoring and dose prediction into one system to allow more optimal administration of MST. In one embodiment, the monitoring system 3 may be linked to control system 5 for locking out stimulation during seizure, locking out stimulation if cardiac rhythmic anomalies occur, determining cortical excitability levels prior to first attempt, determining cortical excitability levels between attempts in order to set the power level for the next attempt, and automatically controlling the ramp up of power level for successive attempts.

Motor Threshold

In general, the strength of field and switching rate should be great enough to exceed twice the motor threshold. The motor threshold represents the minimal strength of field and switching rate needed to cause an evoked potential at the patient's abductor pollicis brevis (APB) muscle (i.e. movement of a patient's thumb) when the corresponding area of the motor cortex is stimulated with a pulsed magnetic field. In accordance with the invention, the location of the right hand motor area and relaxed motor threshold are first identified over the left hemisphere. (See e.g., Epstein C M, Lah J K, Meador K, Weissman J D, Gaitan L E, Dihenia B, *Optimized stimulus parameters for lateralized suppression of speech with magnetic brain stimulation*, Neurology, 1996; 47: 1590-1593, the disclosure of which is fully incorporated herein by reference). During stimulation at a rate of 1 Hz, the stimulation coil is moved across the left central region and the device output is gradually adjusted to locate the point of lowest-intensity activation, followed by the magnetic threshold at that site. This position is then recorded. Determining motor threshold requires approximately 5-10 minutes at the first treatment session and less time in subsequent sessions because the location has already been recorded.

MST Controls

For MST treatment stimulation, the coil is re-positioned, typically over the vertex. In one embodiment, a method of inducing a seizure in a patient comprises applying a magnetic field to the patient using a field strength and switching rate sufficient to produce a seizure in the patient. In this embodiment, at least one burst of a frequency of about 40-60 Hertz is applied over about 2-8 seconds. Alternatively, the burst strength should be great enough to exceed twice the patient's motor threshold.

Alternatively, a ramp-up procedure can be used, where a burst is applied, and if no seizure is induced, the length of the pulse burst is increased. These steps are repeated until a seizure is induced. The ramp-up procedure can be achieved automatically, such as with appropriate software, or manually.

In one embodiment, the control system 5 provides for accurate, real-time control of the pulse generation process, including a system to lock out the pulse generation process if EEG or ECG conditions (as determined by the monitoring system 3) preclude administration of a MST stimulus.

In one embodiment, the control system 5 has the ability to track and display trends of treatment parameters and physiological parameters.

Safety Functions

In one embodiment, the control system 5 provides an alarm if cardiac arrthymias or other anomalies requiring clinical intervention occur (as determined by ECG readings), and also locks out stimulation under these conditions.

In one embodiment, the control system 5 provides a signal if a seizure (as determined by EEG) is in progress, and also locks out stimulation under these conditions.

In one embodiment, the control system 5 provides upper limits to prevent undesirable settings regarding frequency (pulse repetition rate), power level, cortical excitability level, motor threshold or other parameters.

Logging Functions

In one embodiment, the control system 5 further includes recording parameters of the session, such as settings to induce seizure, seizure duration, heart rate, location of the coil, cortical excitability level, prior seizure threshold information, blood pressure, or EEG (or ECG) data.

Power Source

In one embodiment, a power switch 6 is triggered by the control system 5 to apply voltage from a power source 7. In one embodiment, the power switch is a solid state switching device, such as a silicon controlled rectifier ("SCR"), insulated gate bi-polar transistor ("IGBT"), or an insulated gate commutated thyristor ("IGCT"). In this embodiment, the power source 7 includes a large capacitor (e.g. 50-100 micro-Farads) that is charged to 1-2 kV. This results in a sinusoidal pulse of current flowing through a coil 8 as determined by its inductance and resistance, producing a proportional magnetic field applied to the patient.

Coils

In one embodiment, the magnetic field is provided by a coil 8 designed to operate efficiently at pulse repetition rates (20-100 pulses per second) and power levels (1.5-3.0 times the patient's motor threshold level) required for MST. As described with respect to the power source, IGBT and IGCT power switching circuits are particularly suited to optimal operation with these parameters. The simplest coils are circular loops with a magnetic field that is directed orthogonally to the plane of the coil. Ferromagnetic and air core coil designs may be used.

Air Core Coil

In one embodiment, the coil is an air core figure-eight coil such as is commonly used for neurological studies (e.g. Magstim, Medtronic). Similar geometries may be employed that conform readily to the shape of the head (e.g. "Magstim double cone coil"). Air core coils may be used subject to geometry and thermal limitations, well known to those skilled in the art.

For example, MST systems operate at relatively high pulse repetition rates and at high magnetic field flux densities in order to intentionally induce a seizure. This high current level and repetition rate result in significant resistive heating in coils having a large number of turns (e.g. >20), as is the case with air core coils. The shape of the ferromagnetic core can be designed so that the magnetic field is optimized to stimulate the cortical tissue of interest. This is more difficult to accomplish with air core designs since geometric options are limited by the physical volume taken by the windings and the need to place the windings as close to the skull as possible.

Ferromagnetic Core Coil

A ferromagnetic core permits distribution of the windings around the core so that they are not densely packed near the skull, thus freeing up room to more optimally position the poles. Also, due to the improved efficiencies, about one forth the power is required to produce the same magnetic flux density as an equivalent air core coil. Since high power levels are required for MST operation, this gain in efficiency is particularly significant.

An approximately hemispherical ferromagnetic core may be one embodiment, and another embodiment may have a ferromagnetic core including a highly saturable magnetic material having a magnetic saturation of at least 0.5 Tesla. Such ferromagnetic cores are shaped to optimize the magnetic field distribution in the areas most likely to be the locus of a seizure. Some of the cortical structures accessed during MST are deeper (e.g. cingulate gyrus) than tissue typically stimulated in TMS depression treatment. The ferromagnetic core allows efficient localization of the field.

Turning to FIG. 3, in one embodiment, the invention comprises a ferromagnetic core material magnetic stimulation device 10. The device comprises a ferromagnetic core 12 surrounded by windings 14, as will be described. An insulative material 16, is interposed between the core 12 and windings 14. The device 10 also includes a cable 20 for connecting device 10 to a control system (not shown) as previously described. The cable 20 may be covered by a housing 18 for protection and strain relief.

Coils designed using high saturation ferromagnetic core materials are ideally suited to MST since high flux densities can be attained with few windings and the field shape can be manipulated by shaping the iron core for the intended use and treatment depth.

A ferromagnetic core 12 can be fabricated from various ferromagnetic materials such as 3% grain oriented silicon steel or vanadium permendur (also known as supermendur). The material is chosen to have a high saturation level, a sharp-knee B-H curve (i.e. quickly switches from saturated to non-saturated states), low eddy current losses, and a practical cost. The core material must be fabricated into many electrically isolated layers to minimize eddy current losses. The orientation of the lamination must be such as to disrupt the eddy currents (i.e. perpendicular to the direction of induced current flow whenever possible). Also, if the material has a grain orientation, it should be directed parallel to the induced magnetic flux.

The physical shape of the core is determined by the desired shape of the magnetic field between the pole faces. One embodiment for the core shape for stimulation of cortical neurons at a depth of 2-3 centimeters is a torus (having an inner diameter of about 1.3 inches, and outer diameter of about 3.95 inches, a depth of 2.223 inches) with a wedge-shaped section removed leaving an angle between pole faces of about 140 degrees.

Typically 6-10 windings (but as few as necessary) of a conductive wire, are placed around the core material so that magnetic flux is established in the core when current passes through the windings. An electrical insulator is placed between the windings and the core material to prevent shorting between the windings and the core. This is particularly important since peak voltages of 1.5 kVolts are typically applied across the coil. Windings can be made of a solid conductor, stranded conductor, or low loss conductors such as Litz wire in which individual conductors are electrically isolated from each other in a typically flat bundle. Peak current levels can reach over 1000 Amperes so the gauge must be large enough to minimize resistive heating (typically greater than #10 AWG for a stranded conductor). Conductors with circular cross sections are not as efficient as flat cross-section conductors due to the skin effect. The center strands of a circular cross section conductor carry very little current, whereas the current is very nearly equally distributed through out the conductive material in a flat conductor. Litz wire is also very efficient due to its flat cross section, but the incremental efficiency is small compared to the increased cost and more difficult manufacturing processes. Also, flat wire allows very efficient winding and packaging. Therefore one embodiment includes flat solid copper with current carrying capacity equivalent to #8AWG. The flat wire is soldered to lead wires (typically flexible stranded copper) for remote connection to the stimulator drive circuit.

When the windings are pulsed with high current, a hoop stress is induced in the windings that would tend to result in physical movement of the conductor. For this reason the windings are epoxied in place with an epoxy that has high tensile strength and good thermal conductivity so as to conduct any heat generated due to resistive heating or eddy currents to the outside surfaces of the coil assembly.

The ferromagnetic core can be fabricated by spooling a ribbon (typically 12-14 mil thick) of the selected ferromagnetic substrate that is coated with an insulator to electrically isolate laminations, into a torus. The wound spool may be epoxy impregnated or tack welded to mechanically stabilize it for further processing. A wedge is cut from the torus to create the two pole faces. The cutting process may short circuit laminations together, so the cut core is soaked in a phosphoric acid bath for about an hour to etch away the burrs. Resistance is measured between laminations to guarantee appropriate etching. The cut core is taped with mylar (or other insulator) to provide an insulating barrier. Mechanical brackets are typically added at this point to provide a means of mechanically attaching to the finished coil. Flat wire is then wound helically around the core taking care that the windings are placed in their desired locations. Lead wires are soldered to each end of the flat wire. The wound core assembly is then epoxy dipped, coated or impregnated to mechanically bond the windings in place. After curing, the assembly is ready for test and final assembly with an enclosure.

In another embodiment, the ferromagnetic core is according to U.S. Pat. No. 6,132,361 and U.S. Pat. No. 5,725,471, the entire disclosures of which are hereby incorporated by reference in their entireties. The coils induce electric fields similar in distribution to those from a MAGSTIM figure-eight coil, however, these coils are much smaller and more efficient, requiring no special cooling.

The invention includes a method for treating a patient, comprising applying a magnetic field to the patient using an approximately hemispherical magnetic core having a magnetic saturation of at least 0.5 Tesla, wherein the strength of the field and switching rate is sufficient to produce a seizure in the patient.

Moreover, the invention further includes a method for producing a seizure in a patient, comprising applying to the patient a magnetic field of strength sufficient to produce a seizure given the switching rate using an approximately hemispherical magnetic core having a magnetic saturation of at least 0.5 Tesla.

Coil Positioner

Returning to FIG. 1, in one embodiment, the coil 8 may be positioned with a coil positioner 9. The coil positioner is a subsystem that aids the operator in placing the coil at the proper location on the patient, supporting the weight of the coil, and maintaining the coil position throughout the MST procedure. The coil positioner may be mechanical, electromechanical, robotic, and may employ optical, magnetic, or video alignment methods. In one embodiment, the device may be positioned and held in place according to the methods of U.S. application Ser. No. 10/752,164, filed Jan. 6, 2004, entitled "Method And Apparatus For Coil Positioning For TMS Studies" incorporated herein by reference as if reproduced in its entirety.

In one embodiment, the system 1 further comprises a support mechanism (not shown).

In one embodiment, the system 1 further comprises system for noise reduction. MST stimulation levels produce acoustic noise that exceeds desirable levels. In one embodiment, the system 1 incorporates coil designs that reduce this noise by encasing the coil in a vacuum or partial vacuum cavity and removing heat through heat sinks and circulation of fluids (including ferrofluids) to an area where the heat can be radiated to the ambient environment. Headphones and earplugs may also be provided to aid in reducing patient exposure to excessive acoustic noise.

In one embodiment, the system 1 further comprises patient positioning aids, including a chair and positioning pads.

The useful dosage to be administered will vary depending upon such factors as age, weight, thickness of hair, and particular region to be treated, as well as the therapeutic or diagnostic use contemplated, as will be readily apparent to those skilled in the art. Typically, dosage is administered at lower levels and increased until the desirable effect is achieved.

Figure 4:
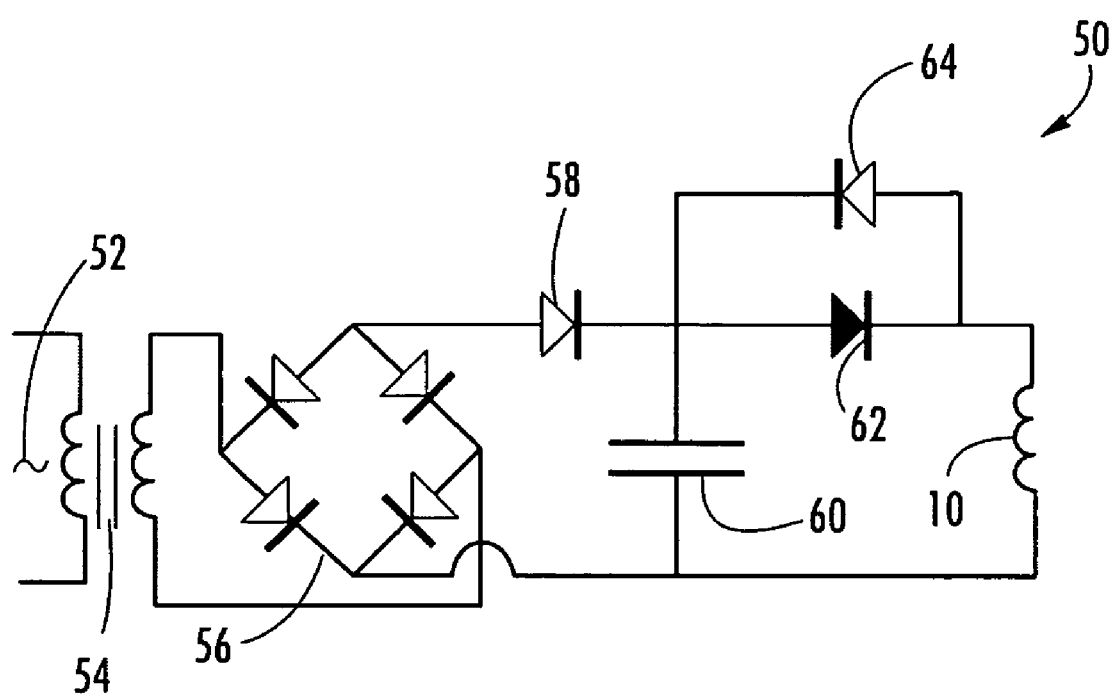
FIG. 4 is a schematic of the electrical circuit used to stimulate the device.

FIG. 4 shows an electrical circuit 50 used to "fire" the device 40 (FIGS. 6 and 6A). A normal 120 volt, 60 Hz signal excites the circuit at 52. A transformer 54 amplifies the voltage up to about 1-3 kV. This high voltage AC signal is then fed into a full wave rectifier bridge 56. The signal from the rectifier bridge 56 is then passed through a diode 58 to charge a capacitor 60. The purpose of all the electrical components to the left or upstream of the capacitor 60 is to put charge into the capacitor 60. The energy residing in the circuit 50, which will be pumped into the device 40, is one-half C (the capacitance value) times the voltage squared.

When thyristor 62 is triggered with a small control voltage pulse, current flows through the thyristor and into the magnetic core 10. In one embodiment, the thyristor 62 is a field controlled thyristor ("FCT"). In one embodiment, the thyristor 62 is an insulated gate bi-polar transistor ("IGBT") or an insulated gate commutated thyristor ("IGCT") to improve the frequency to levels equal to or greater than 100 Hz.

Most of this energy goes back into the capacitor 60, recharging it in the opposite polarity from its initial charge. The reverse charged capacitor 60 immediately discharges again through the magnetic core 10 through diode 64, connected in parallel. Theoretically, all of this energy should pass into capacitor 60 to recharge it according to its initial polarity. In practice, of course, this LC circuit has some loss, and the thyristor 62 does not shutoff immediately. Two to three exponentially decaying ring cycles of this L circuit are witnessed in practice before current of magnetic core 10 is completely shut off. After shutoff, the capacitor 60 charges through diode 58 as it did initially. It continues to charge until thyristor 62 is triggered again.

The circuit shown is just one embodiment for the practice of this invention but other circuit designs (such as a dual capacitor arrangement or so forth) may be used to fire the magnetic core as well, as will be apparent to those skilled in the art.

The invention is further described in the following example.

A patient in need of MST is treated as follows. The patient undergoes a pretreatment medical examination that includes a history, physical, neurologic examination, ECG, and laboratory tests. Medications that affect the seizure threshold are noted and decreased or discontinued when clinically feasible. Monoamine Oxidase (MAO) inhibitors are discontinued 2 weeks before treatment, and the patient is essentially lithium-free. Severe hypertension is controlled before beginning treatment. Patients with compromised cardiovascular status should be evaluated and monitored closely.

The MST treatment is given in the early morning after an 8- to 12-hour period of fasting. Oral and hearing protection is provided. Atropine or another anticholinergic agent is given prior to the treatment. An intravenous line is placed in a peripheral vein, and access to this vein is maintained until the patient is fully recovered. The anesthetic methohexital is given first, followed by succinylcholine for muscle relaxation. Ventilatory assistance is provided with a positive pressure bag using 100 percent oxygen. The EEG, ECG, blood pressure, and pulse rate should be monitored throughout the procedure. Stimulus devices may be placed either bifronto-temporally (bilateral) or unifrontotemporally (unilateral). Bilateral MST may be more effective in certain patients or conditions, although unilateral MST, particularly on the non-dominant side, may be preferable.

Seizure threshold varies greatly among patients and may be difficult to determine; nevertheless, the lowest amount of energy to induce an adequate seizure should be used. This can be accomplished by determining the motor threshold and the applying a strength greater than twice the motor threshold, or by applying a ramp-up method.

The magnetic flux density created by the coil is from about 0.1 to 2 Teslas. The frequency is 5 Hz to 120 Hz, normally 40 Hz to 60 Hz, or over 100 Hertz. The burst duration is in the range of 0.1 to 60 seconds, or about 2 to 8 seconds.

Seizure monitoring may be accomplished by an EEG or by the "cuff" technique, where a blood pressure cuff is placed on an arm or leg and is inflated above systolic pressure prior to the injection of a muscle relaxing agent. In unilateral MST, the cuff should be on the same side as the coil to ensure that a bilateral seizure occurred.

The number of treatments in a course of therapy varies. Six to twelve treatments are usually effective. In one embodiment, treatments are given three times weekly.

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed:

1. A system for performing magnetic seizure therapy on a patient in need thereof, comprising:
   a magnetic coil;
   a power switch for applying a pulse of electrical current to the magnetic coil such that the induced current density in the magnetic coil is sufficient to cause a seizure in the patient;
   a monitoring device for monitoring the patient; and
   a control device for adjusting a magnetic field created by the magnetic coil in a predictive manner, increasing the magnetic field until sufficient to produce the seizure in the patient and for preventing further stimulation when a seizure is in progress.

2. The system of claim 1, wherein the monitoring device includes at least one of an EEG monitor, an ECG monitor, a blood pressure monitor, and a heart rate monitor.

3. The system of claim 1, wherein the control device prevents further stimulation by interrupting the flow of current to the magnetic coil.

4. The system of claim 1, wherein the control device prevents further stimulation by shielding the patient from the magnetic field.

5. The system of claim 1, wherein the control device prevents further stimulation by moving the coil a sufficient distance away from the patient to prevent stimulation.

6. The system of claim 1, wherein the pulse is part of a burst applied over a range of about 2 to about 8 seconds.

7. The system of claim 6, wherein the burst is applied with a pulse repetition rate of about 40 to about 60 Hertz.

8. The system of claim 6, wherein the burst is applied with a pulse repetition rate of over 100 Hertz.

9. The system of claim 6, further comprising a second burst separated from the burst by a waiting period of less than one minute.

10. The system of claim 1, further comprising a device for recording parameters of the therapy.

11. The system of claim 1, wherein the control device provides a signal for indicating the occurrence of a seizure.

12. The system of claim 1, wherein the magnetic coil is an approximately hemispherical magnetic core having a magnetic saturation of at least 0.5 Tesla.

13. The system of claim 1, wherein the control device further comprises a feedback circuit that adjusts a magnetic field created by the magnetic coil.

14. The system of claim 13, wherein the feedback circuit adjusts a pulse repetition rate.

15. The system of claim 13, wherein the feedback circuit adjusts a burst length.

16. The system of claim 13, wherein the feedback circuit adjusts a flux density.

17. The system of claim 1, further comprising a computer processing device for analyzing a signal provided by the monitoring device.

18. The system of claim 17, wherein the processing device compares a measured cortical excitability of a patient with a cortical excitability reflective of a seizure.

19. The system of claim 18, wherein the cortical excitability reflective of a seizure is a predetermined EEG signal.

20. The system of claim 18, wherein the measured cortical excitability of a patient is a function of EEG signals.

21. The system of claim 17, wherein the processing device provides a signal to a feedback circuit that adjusts a magnetic field created by the magnetic coil.

22. The system of claim 17, wherein the processing device provides a signal to a display device to allow a magnetic field created by the magnetic coil to be manually adjusted.

23. A method for treating a patient, comprising:
applying a magnetic field to the patient;
adjusting the magnetic field in a predictive manner, increasing the magnetic field until sufficient to produce a seizure in the patient; and
preventing further stimulation from the field when a seizure is in progress.

24. The method of claim 23, further comprising determining at least one of the following: if the patient is in a resting state, a pre-seizure state, in seizure, and a post-seizure state.

25. The method of claim 24, further comprising recording parameters that induce a seizure in the patient.

26. The method of claim 24, further comprising providing a silicon controlled rectifier, insulated gate bi-polar transistor, and an insulated gate commutated thyristor for applying voltage.

27. The method of claim 23, further comprising monitoring the patient.

28. The method of claim 27, further comprising analyzing a signal provided by the monitoring.

29. The method of claim 28, wherein the analyzing comprises comparing a measured cortical excitability of a patient with a cortical excitability reflective of a seizure.

30. The method of claim 29, wherein the measured cortical excitability of a patient is a function of EEG signals.

31. The method of claim 29, wherein the cortical excitability reflective of a seizure is a predetermined EEG signal.

32. The method of claim 28, further comprising adjusting a magnetic field created by the magnetic coil as a function of the analyzing.

33. The method of claim 28, further comprising displaying an indication of the analyzing to allow a magnetic field created by the magnetic coil to be adjusted.

34. The method of claim 27, wherein monitoring includes at least one of EEG monitoring, ECG monitoring, blood pressure monitoring, and heart rate monitoring.

35. The method of claim 23, further comprising recording parameters of the therapy.

36. The method of claim 35, wherein the parameters include at least one of: settings to induce seizure, seizure duration, heart rate, blood pressure, ECG data and EEG data.

37. The method of claim 23, further comprising adjusting a pulse of electrical current to a magnetic coil.

38. The method of claim 37, wherein the pulse is part of a burst.

39. The method of claim 38, wherein the burst is applied over a range of about 2 to about 8 seconds.

40. The method of claim 38, wherein the burst is applied with a pulse repetition rate of about 40 to about 60 Hertz.

41. The method of claim 38, wherein the burst is applied with a pulse repetition rate of over 100 Hertz.

42. The method of claim 38, further comprising a second burst separate from the burst by a waiting period.

43. The method of claim 42, wherein the waiting period is less than one minute.

44. The method of claim 42, further comprising setting the waiting period to a fixed interval.

45. The method of claim 42, further comprising automatically controlling the ramp up of power level for successive bursts.

46. The method of claim 38, further comprising determining cortical excitability levels prior to the burst.

47. The method of claim 38, further comprising determining cortical excitability levels between bursts.

48. The method of claim 47, further comprising adjusting the power level for the next burst.

49. The method of claim 38, wherein the burst is applied with a pulse repetition rate of 60 to 100 Hertz.

50. The method of claim 37, wherein the induced current density as a result of the pulse creates a magnetic field sufficient to cause a seizure in the patient.

51. The method of claim 23, wherein the magnetic field is adjusted as a function of a pulse repetition rate.

52. The method of claim 23, wherein the magnetic field is adjusted as a function of burst length.

53. The method of claim 23, wherein the magnetic field is adjusted as a function of a flux density.

54. A method for producing a seizure in a patient, comprising applying to the patient a magnetic field of strength and adjusting the magnetic field in a predictive manner, increasing the magnetic field until sufficient to produce a seizure using an approximately hemispherical magnetic core having a magnetic saturation of at least 0.5 Tesla, and preventing further stimulation from the field when a seizure is in progress.

* * * * *